US012657881B2

(12) United States Patent
Aghdam et al.

(10) Patent No.: US 12,657,881 B2

(45) Date of Patent: Jun. 16, 2026

(54) SYSTEMS AND METHODS FOR PROCESSING ELECTRONIC IMAGES FOR AUTO-LABELING FOR COMPUTATIONAL PATHOLOGY

(71) Applicant: PAIGE.AI, INC., New York, NY (US)

(72) Inventors: Hamed Aghdam, New York, NY (US); Christopher Kanan, Pittsford, NY (US)

(73) Assignee: Paige.AI, Inc., New York, NY (US)

( * ) Notice: Subject to any disclaimer, the term of this patent is extended or adjusted under 35 U.S.C. 154(b) by 545 days.

(21) Appl. No.: 18/161,752

(22) Filed: Jan. 30, 2023

(65) Prior Publication Data

US 2023/0245430 A1 Aug. 3, 2023

Related U.S. Application Data

(60) Provisional application No. 63/305,125, filed on Jan. 31, 2022.

(51) Int. Cl.
| | |
|---|---|
| *G06V 10/774* | (2022.01) |
| *G06T 7/00* | (2017.01) |
| *G06T 7/11* | (2017.01) |
| *G06V 10/764* | (2022.01) |

(Continued)

(52) U.S. Cl.
CPC .......... *G06V 10/774* (2022.01); *G06T 7/0012* (2013.01); *G06T 7/11* (2017.01); *G06V 10/764* (2022.01); *G06V 20/70* (2022.01); *G16H 30/40* (2018.01); *G06T 2207/20081* (2013.01); *G06T 2207/30024* (2013.01); *G06T 2207/30081* (2013.01); *G06V 2201/03* (2022.01)

(58) Field of Classification Search
CPC .............................. G16H 30/40; G06V 20/70
See application file for complete search history.

(56) References Cited

U.S. PATENT DOCUMENTS

| | | |
|---|---|---|
| 2022/0005201 A1 | 1/2022 | Rothrock et al. |
| 2022/0309653 A1* | 9/2022 | Hassanpour ........... G06V 10/82 |

OTHER PUBLICATIONS

Wang et al, "Embracing the disharmony in medical imaging: A Simple and effective framework for domain adaptation", 2021, pp. 1-15, Medical image analysis (Year: 2021).*

(Continued)

*Primary Examiner* — Edward Park

(74) *Attorney, Agent, or Firm* — Bookoff McAndrews, PLLC

(57) ABSTRACT

Systems and methods are described herein for processing electronic medical images to determine a first machine learning system, the first machine learning system having been trained to identify regions of electronic medical images; receive a plurality of electronic medical images, each of the electronic medical images being associated with one or more subcategories; determine a subset of the plurality of electronic medical images that are associated with only one subcategory of the one or more subcategories; provide the subset of the plurality of electronic medical images to the first machine learning system, the first machine learning system identifying regions within the subset of the plurality of electronic medical images associated with the subcategory; and train a second machine learning system, using the identified regions and the subset of the plurality of electronic medical images.

20 Claims, 15 Drawing Sheets

(51) Int. Cl.
  *G06V 20/70* (2022.01)
  *G16H 30/40* (2018.01)

(56) References Cited

OTHER PUBLICATIONS

Kalapahar, et al, "Gleason Grading of Histology Prostate Images Through Semantic Segmentation via Residual U-Net", 2020, pp. 2501-2505, IEEE (Year: 2020).*

Lucas et al, "Deep learning for automatic Gleason pattern classification for grade group determination of prostate biopsies", Virchows Archiv, 2019, pp. 77-83 (Year: 2019).*

Nagpal et al, "Development and Validation of a Deep Learning Algorithm for Gleason Grading of Prostate Cancer From Biopsy Specimens", Jama Oncology, pp. 1372-1380, 2020 (Year: 2020).*

An et al, "Hierarchical deep learning models using transfer learning for disease detection and classification based on small number of medical images", 2021, pp. 1-9, Nature Portfolio (Year: 2021).*

Bulten, Wouter, et al. "Supplementary Appendix to Automated deep-learning system for Gleason grading of prostate cancer using biopsies: a diagnostic study." The Lancet Oncology 21.2 (2020): 233-241.

Bulten, Wouter, et al. "Automated deep-learning system for Gleason grading of prostate cancer using biopsies: a diagnostic study." The Lancet Oncology 21.2 (2020): 233-241.

* cited by examiner

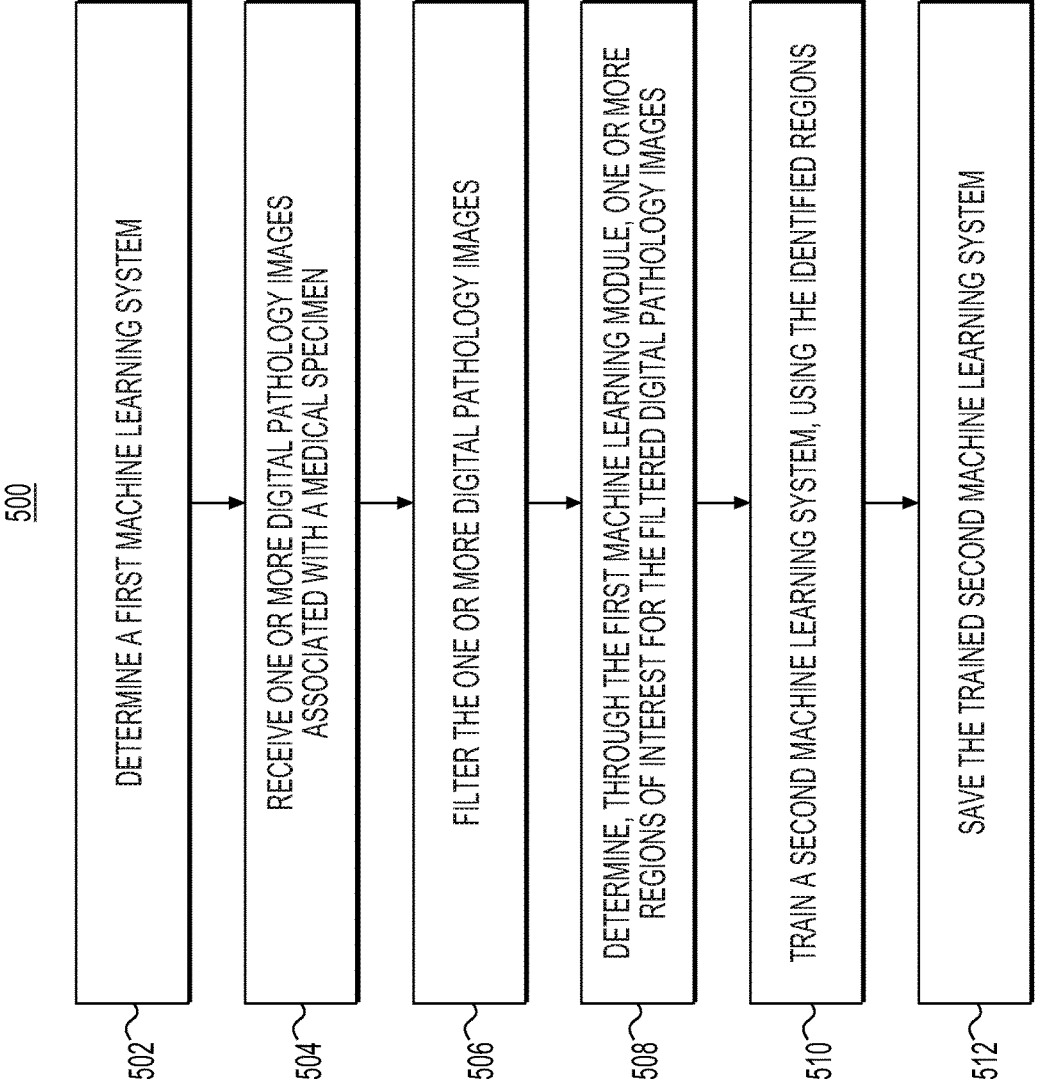

500

502 — DETERMINE A FIRST MACHINE LEARNING SYSTEM

504 — RECEIVE ONE OR MORE DIGITAL PATHOLOGY IMAGES ASSOCIATED WITH A MEDICAL SPECIMEN

506 — FILTER THE ONE OR MORE DIGITAL PATHOLOGY IMAGES

508 — DETERMINE, THROUGH THE FIRST MACHINE LEARNING MODULE, ONE OR MORE REGIONS OF INTEREST FOR THE FILTERED DIGITAL PATHOLOGY IMAGES

510 — TRAIN A SECOND MACHINE LEARNING SYSTEM, USING THE IDENTIFIED REGIONS

512 — SAVE THE TRAINED SECOND MACHINE LEARNING SYSTEM

552 RECEIVE ONE OR MORE DIGITAL PATHOLOGY IMAGES ASSOCIATED WITH A MEDICAL SPECIMEN

554 DETERMINE, USING A TRAINED MACHINE LEARNING SYSTEM, ONE OR MORE REGIONS OF ONE OR MORE SUB-CATEGORIES ON THE DIGITAL PATHOLOGY IMAGES

556 OUTPUT A SEGMENTATION MAP

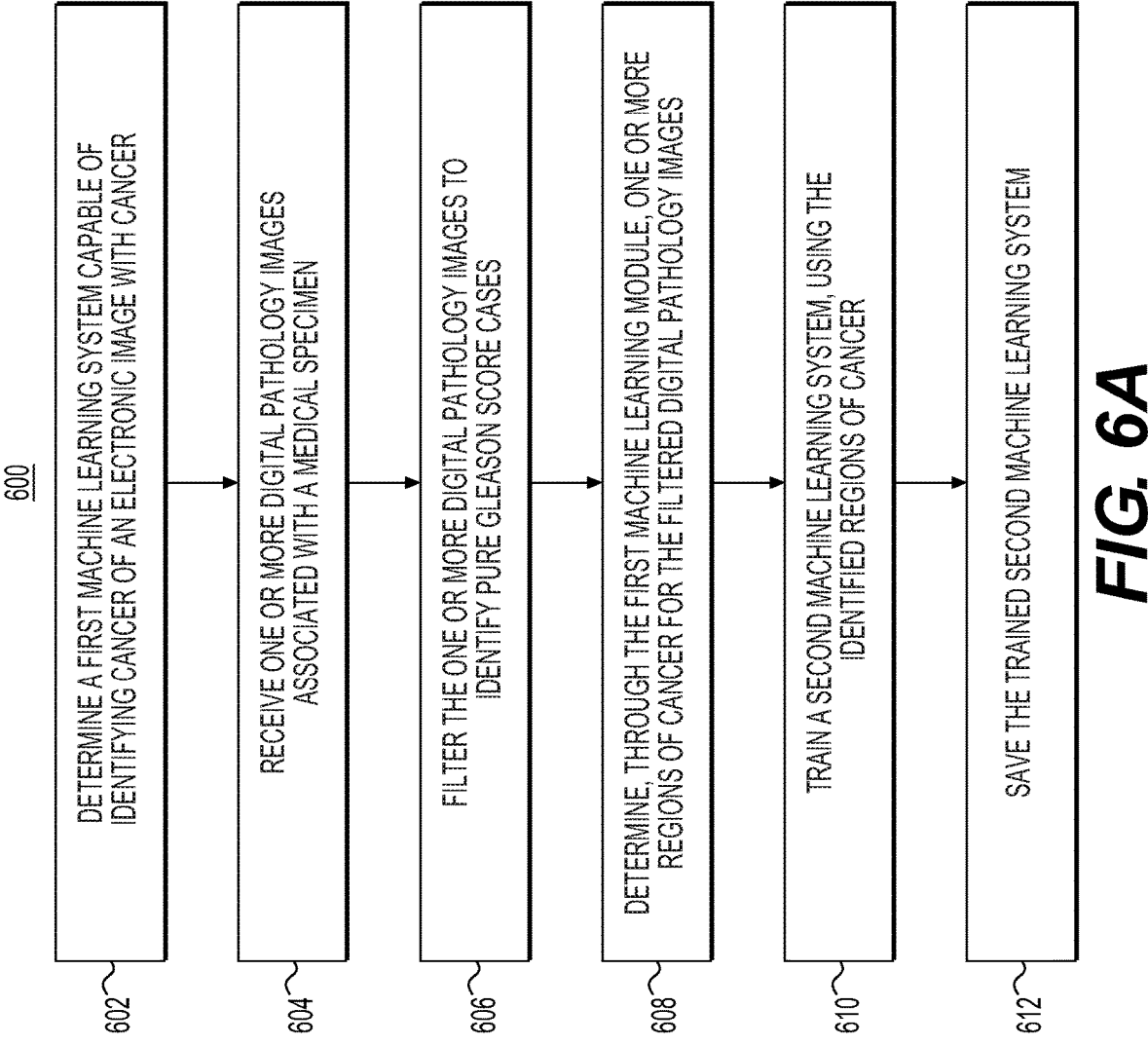

600

602 — DETERMINE A FIRST MACHINE LEARNING SYSTEM CAPABLE OF IDENTIFYING CANCER OF AN ELECTRONIC IMAGE WITH CANCER

604 — RECEIVE ONE OR MORE DIGITAL PATHOLOGY IMAGES ASSOCIATED WITH A MEDICAL SPECIMEN

606 — FILTER THE ONE OR MORE DIGITAL PATHOLOGY IMAGES TO IDENTIFY PURE GLEASON SCORE CASES

608 — DETERMINE, THROUGH THE FIRST MACHINE LEARNING MODULE, ONE OR MORE REGIONS OF CANCER FOR THE FILTERED DIGITAL PATHOLOGY IMAGES

610 — TRAIN A SECOND MACHINE LEARNING SYSTEM, USING THE IDENTIFIED REGIONS OF CANCER

612 — SAVE THE TRAINED SECOND MACHINE LEARNING SYSTEM

652 — RECEIVE ONE OR MORE DIGITAL PATHOLOGY IMAGES ASSOCIATED WITH A MEDICAL SPECIMEN

654 — DETERMINE, USING A TRAINED MACHINE LEARNING SYSTEM, ONE OR MORE REGIONS OF ONE OR MORE GLEASON SCORES ON THE DIGITAL PATHOLOGY IMAGES

656 — OUTPUT A SEGMENTATION MAP

GLEASON PATTERN 3
GLEASON PATTERN 4
GLEASON PATTERN 5

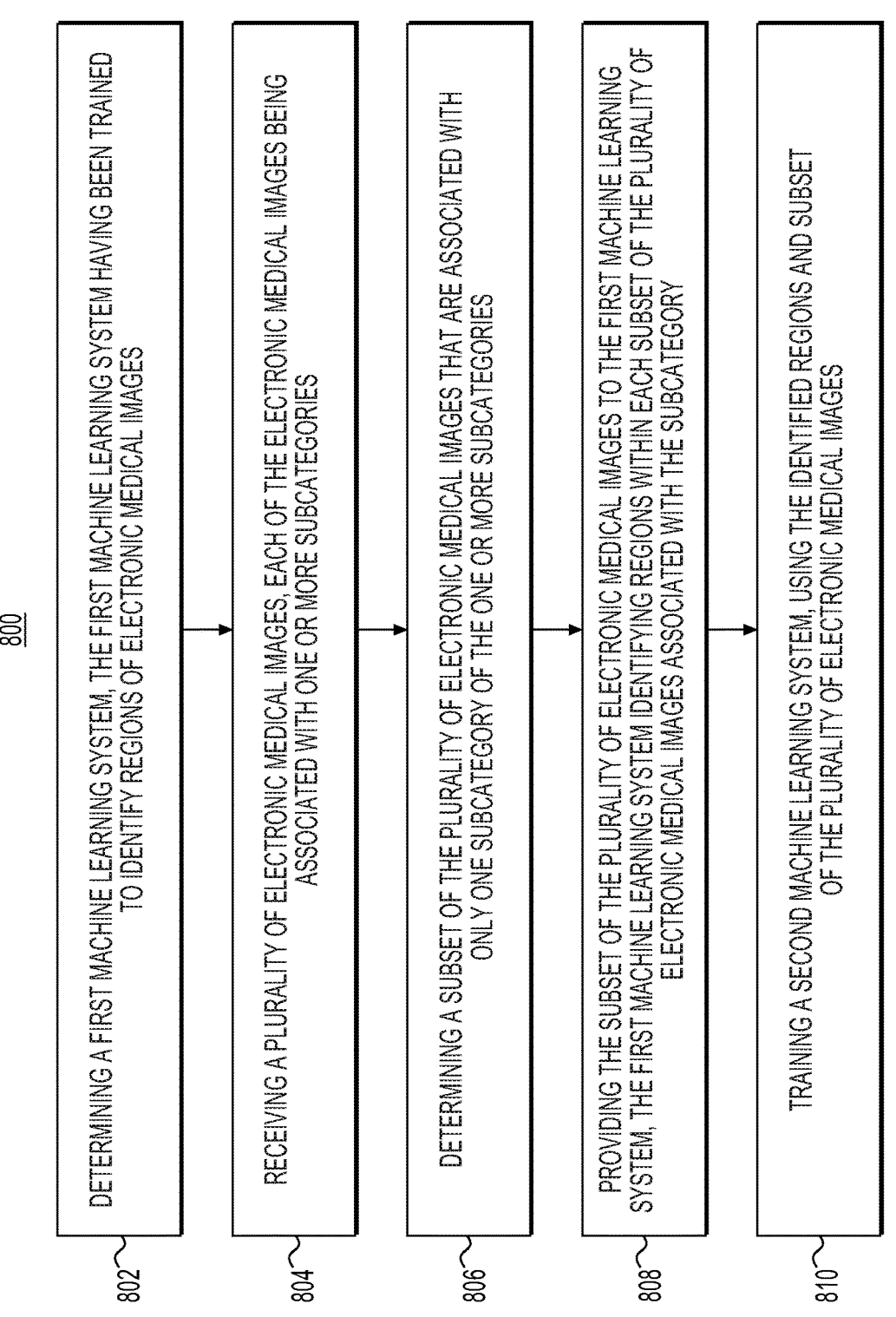

800

802 — DETERMINING A FIRST MACHINE LEARNING SYSTEM, THE FIRST MACHINE LEARNING SYSTEM HAVING BEEN TRAINED TO IDENTIFY REGIONS OF ELECTRONIC MEDICAL IMAGES

804 — RECEIVING A PLURALITY OF ELECTRONIC MEDICAL IMAGES, EACH OF THE ELECTRONIC MEDICAL IMAGES BEING ASSOCIATED WITH ONE OR MORE SUBCATEGORIES

806 — DETERMINING A SUBSET OF THE PLURALITY OF ELECTRONIC MEDICAL IMAGES THAT ARE ASSOCIATED WITH ONLY ONE SUBCATEGORY OF THE ONE OR MORE SUBCATEGORIES

808 — PROVIDING THE SUBSET OF THE PLURALITY OF ELECTRONIC MEDICAL IMAGES TO THE FIRST MACHINE LEARNING SYSTEM, THE FIRST MACHINE LEARNING SYSTEM IDENTIFYING REGIONS WITHIN EACH SUBSET OF THE PLURALITY OF ELECTRONIC MEDICAL IMAGES ASSOCIATED WITH THE SUBCATEGORY

810 — TRAINING A SECOND MACHINE LEARNING SYSTEM, USING THE IDENTIFIED REGIONS AND SUBSET OF THE PLURALITY OF ELECTRONIC MEDICAL IMAGES

*FIG. 8*

SYSTEMS AND METHODS FOR PROCESSING ELECTRONIC IMAGES FOR AUTO-LABELING FOR COMPUTATIONAL PATHOLOGY

RELATED APPLICATION(S)

This application claims priority to U.S. Provisional Application No. 63/305,125 filed Jan. 31, 2022, the entire disclosure of which is hereby incorporated herein by reference in its entirety.

FIELD OF THE DISCLOSURE

Various embodiments of the present disclosure pertain generally to image processing. More specifically, particular embodiments of the present disclosure relate to systems and methods for processing electronic images for auto-labeling for computational pathology.

BACKGROUND

The first step in analyzing a whole slide image (WSI) of a biopsy or resection may be to determine if cancerous regions are present in the WSI. The next step may be studying cancerous regions and grading the cancer within the WSI. Grading may be done by dividing cancerous regions into more granular categories. For instance, prostate cancer has nine distinct grades where each grade could be a combination of up to three different cancer severity scores. Three out of nine categories are pure cases where the entire cancerous region has the same grade (e.g., a Gleason score of 3+3). Overall, classifying a WSI as benign or cancerous has produced accurate results, whereas grading cancerous regions may be considered challenging and subjective. Grading cancer is more challenging because cancerous regions may have many different visual patterns compared to benign regions. When grading cancer, the margin between consecutive grades of cancer may be difficult to discern.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for processing electronic medical images, comprising: determine a first machine learning system, the first machine learning system having been trained to identify regions of electronic medical images; receive a plurality of electronic medical images, each of the electronic medical images being associated with one or more subcategories; determine a subset of the plurality of electronic medical images that are associated with only one subcategory of the one or more subcategories; provide the subset of the plurality of electronic medical images to the first machine learning system, the first machine learning system identifying regions within the subset of the plurality of electronic medical images associated with the subcategory; and train a second machine learning system, using the identified regions and the subset of the plurality of electronic medical images.

A system for processing electronic digital medical images, the system including: determine a first machine learning system, the first machine learning system having been trained to identify regions of electronic medical images; receive a plurality of electronic medical images, each of the electronic medical images being associated with one or more subcategories; determine a subset of the plurality of electronic medical images that are associated with only one subcategory of the one or more subcategories; provide the subset of the plurality of electronic medical images to the first machine learning system, the first machine learning system identifying regions within the subset of the plurality of electronic medical images associated with the subcategory; and train a second machine learning system, using the identified regions and the subset of the plurality of electronic medical images.

A non-transitory computer-readable medium storing instructions that, when executed by a processor, perform operations processing electronic digital medical images, the operations including: determine a first machine learning system, the first machine learning system having been trained to identify regions of electronic medical images; receive a plurality of electronic medical images, each of the electronic medical images being associated with one or more subcategories; determine a subset of the plurality of electronic medical images that are associated with only one subcategory of the one or more subcategories; provide the subset of the plurality of electronic medical images to the first machine learning system, the first machine learning system identifying regions within the subset of the plurality of electronic medical images associated with the subcategory; and train a second machine learning system, using the identified regions and the subset of the plurality of electronic medical images.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 5A is a flowchart illustrating an example method for training a system to auto-label digital medical images, according to one or more embodiments.

FIG. 6A is a flowchart illustrating an example method for training a system to auto-label Gleason pattern localization on digital medical images, according to one or more embodiments.

FIG. 8 is a flowchart illustrating an example method for auto-labeling digital medical images to create training images for a machine learning system.

DESCRIPTION OF THE EMBODIMENTS

Figure 1A:
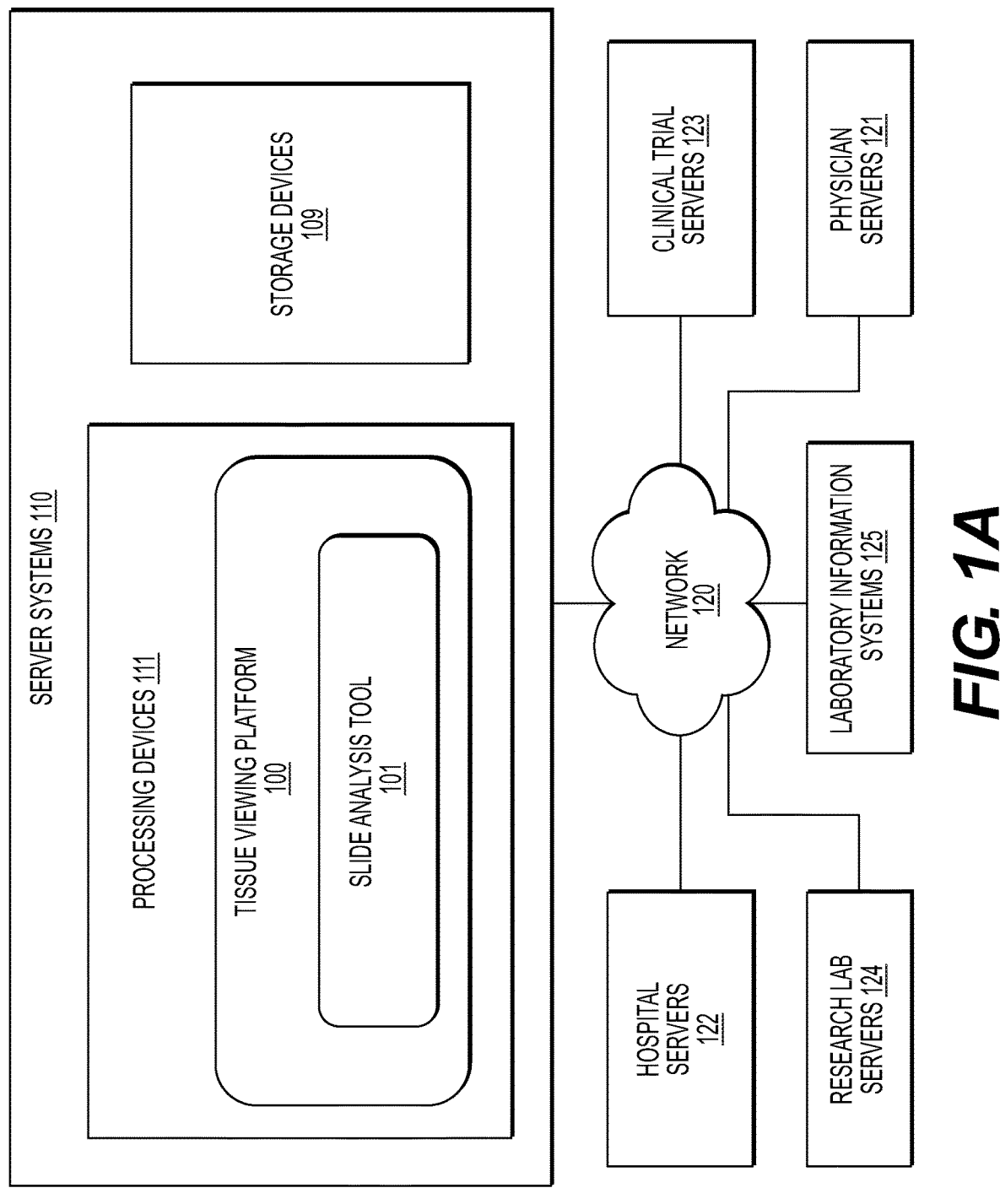
FIG. 1A illustrates an exemplary block diagram of a system and network for processing images to determine auto-labeling for training images, according to techniques presented herein.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

As used herein, a "machine learning model" generally encompasses instructions, data, and/or a model configured to receive input, and apply one or more of a weight, bias, classification, or analysis on the input to generate an output. The output may include, for example, a classification of the input, an analysis based on the input, a design, process, prediction, or recommendation associated with the input, or any other suitable type of output. A machine learning model is generally trained using training data, e.g., experiential data and/or samples of input data, which are fed into the model in order to establish, tune, or modify one or more aspects of the model, e.g., the weights, biases, criteria for forming classifications or clusters, or the like. Deep learning techniques may also be employed. Aspects of a machine learning model may operate on an input linearly, in parallel, via a network (e.g., a neural network), or via any suitable configuration.

The execution of the machine learning model may include deployment of one or more machine learning techniques, such as linear regression, logistical regression, random forest, gradient boosted machine (GBM), deep learning, and/or a deep neural network. Supervised and/or unsupervised training may be employed. For example, supervised learning may include providing training data and labels corresponding to the training data, e.g., as ground truth. Unsupervised approaches may include clustering, classification or the like. K-means clustering or K-Nearest Neighbors may also be used, which may be supervised or unsupervised. Combinations of K-Nearest Neighbors and an unsupervised cluster technique may also be used. Any suitable type of training may be used, e.g., stochastic, gradient boosted, random seeded, recursive, epoch or batch-based, etc.

Annotating segmentation masks in digital medical/pathology images (e.g., a WSI) manually may be a time-consuming process. Further, this process may require human experts with deep domain knowledge. Drawing segmentation masks may become more challenging on WSIs with multiple classes present (e.g., different cancer grades). Human-in-the-loop approaches to annotating segmentation masks may attempt to reduce the cost by repeatedly asking human experts to partially correct errors or to draw coarse segmentation masks. Hidden costs of human-in-the-loop approaches may increase the overall cost of annotation. Auto-labeling, as described in the system herein, offers an effective solution to generate segmentation masks for specific target tasks. In particular, the system herein may use a model (such as a machine learning system) that is built for another related task to help create training images. Auto-labeling may refer to the process of utilizing a particular model or computer algorithm to identify and/or map subcategories of an image. Auto-labeling may output segmentation masks. These segmentation masks may then be utilized to more effectively train machine learning systems.

One technique for building more accurate grading systems (e.g., cancer grading system) may be to obtain segmentation masks of different grades, but, creating these can be time-consuming, costly, and a subjective task.

FIG. 1A illustrates an exemplary block diagram of a system and network for processing images to determine auto-labeling for training images, according to techniques presented herein. Specifically, FIG. 1A illustrates server systems 110 that include various processing devices 111 (e.g., a tissue viewing platform 100 that includes a slide analysis tool 101) and storage devices 109, a network 120, physician servers 121, hospital servers 122, clinical trial servers 123, research lab servers 124, and laboratory information systems 125.

The server systems 110 may include one or more interconnected systems of server devices (e.g., multiple interconnected datacenters or cloud networks, multiple interconnected systems within a datacenter or a cloud network, etc.). Server systems 110 may include one or more storage devices 109 (e.g., digital and/or electronic storage devices 109) for storing images and data received from at least one of the physician servers 121, the hospital servers 122, the clinical trial servers 123, the research lab servers 124, and/or the laboratory information systems 125. The server systems 110 may also include processing devices for processing images and data stored in the one or more storage devices 109. For example, the server systems 110 may include processing devices that are configured to implement the tissue viewing platform 100. The tissue viewing platform 100 may use the slide analysis tool 101 to analyze tissues in a WSI.

The server systems 110 may further include one or more machine learning tool(s) or capabilities. For example, the processing devices may include a machine learning tool for the tissue viewing platform 100 (e.g., the processing devices may run one or more trained machine learning models). In certain embodiments, a portion or all of the operations performed by the processing devices may be performed on a local processing device (e.g., a desktop computer, a laptop computer, a mobile phone, a tablet, etc.).

The network 120 may include one or more wired and/or wireless networks, such as the Internet, an intra-net, a cellular network (e.g., a Third Generation Partnership Project (3GPP) 3G network, 4G network 5G network, etc.), a wide area network (WAN), a local area network (LAN), a public land mobile network (PLMN), and/or the like. The network 120 may be connected to servers, e.g., at hospitals, laboratories, doctors' offices, etc. For example, the physician servers 121, the hospital servers 122, the clinical trial servers 123, the research lab servers 124, and/or the laboratory information systems 125, etc., may each be connected to the network 120, such as the Internet, through one or more computers, servers, and/or handheld mobile devices. According to an example embodiment of the present disclosure, the network 120 may also be connected to the server systems 110.

The physician servers 121, the hospital servers 122, the clinical trial servers 123, the research lab servers 124, and/or the laboratory information systems 125 may include one or more server devices (e.g., in a datacenter or distributed in a cloud network). The physician servers 121, the hospital servers 122, the clinical trial servers 123, the research lab servers 124, and/or the laboratory information systems 125 may create or otherwise obtain images of one or more patients' cytology specimen(s), histopathology specimen(s), slide(s) of the specimen(s), digitized images of the slide(s) of the specimen(s), or any combination thereof. The physician servers 121, the hospital servers 122, the clinical trial servers 123, the research lab servers 124, and/or the laboratory information systems 125 may also obtain any combination of patient-specific information, such as age, medical history, cancer treatment history, family history, past biopsy or cytology information, etc. The physician servers 121, the hospital servers 122, the clinical trial servers 123, the research lab servers 124, and/or the laboratory information systems 125 may transmit digitized slide images and/or patient-specific information to the server systems 110 over the network 120.

The physician servers 121, the hospital servers 122, the clinical trial servers 123, the research lab servers 124, and/or the laboratory information systems 125 may provide images of slides for review by a pathologist. In hospital settings, tissue type information may be stored in the laboratory information systems 125. In certain embodiments, electronic images may be processed to determine histopathology quality without needing to access the laboratory information systems 125. Additionally, access to content stored by the laboratory information systems 125 may be limited due to its sensitive nature.

Figure 1B:
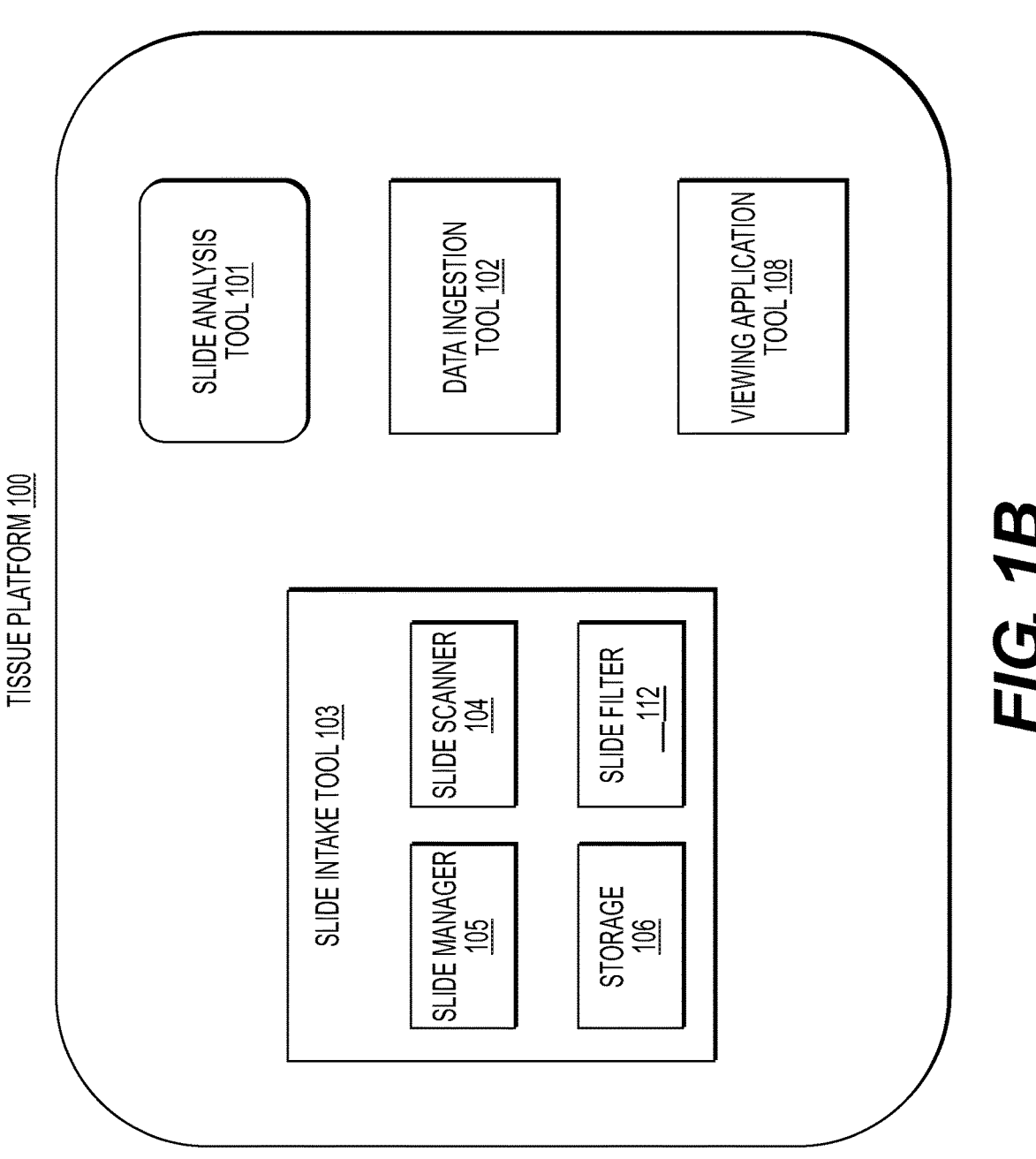
FIG. 1B illustrates an exemplary block diagram of a tissue viewing platform according to techniques presented herein.

FIG. 1B illustrates an exemplary block diagram of the tissue viewing platform of the system of FIG. 1A, according to certain embodiments of the present disclosure. As illustrated in FIG. 1B, the tissue viewing platform 100 may include the slide analysis tool 101, a data ingestion tool 102, a slide intake tool 103 (which may include a slide scanner 104, a slide manager 105, and a storage 106), a viewing application tool 108, and a slide filter 112. The slide analysis tool 101 may include one or more computing devices capable of, e.g., processing electronic images to determine auto-labeled training images. For example, the slide analysis tool 101 may transmit and/or receive digitized slide images and/or patient information to the server systems 110, the physician servers 121, the hospital servers 122, the clinical trial servers 123, the research lab servers 124, and/or the laboratory information systems 125 over the network 120.

The data ingestion tool 102 may include one or more computing devices capable of, e.g., facilitating a transfer of the digital pathology images to various tools, modules, components, and devices described herein that are used for classifying and processing the digital pathology images. The slide intake tool 103 may include one or more computing devices capable of, e.g., scanning pathology images and converting them into a digital form. For example, the slides may be scanned with the slide scanner 104, and the slide manager 105 may process the images on the slides into digitized pathology images and store the digitized images in the storage 106 (e.g., a digital or electronic storage device). The slide filter 112 may be capable of processing electronic images metadata to sort received images by sub-categories present within an image. The viewing application tool 108 may include one or more computing devices capable of, e.g., providing a user (e.g., a pathologist) with specimen property or image property information pertaining to digital pathology image(s). The information may be provided through various output interfaces (e.g., a screen, a monitor, a storage device, a web browser, etc.).

The server systems 110 (not illustrated in FIG. 1B) may store images and data received from the slide analysis tool 101, the data ingestion tool 102, the slide intake tool 103, the slide scanner 104, the slide manager 105, slide filter 112, and/or the viewing application tool 108 (e.g., may store this information in the storage devices 109). The server systems 110 may process the images and data using the processing devices. The server systems 110 may further use one or more machine learning tool(s) or capabilities to process the images and data.

Figure 1C:
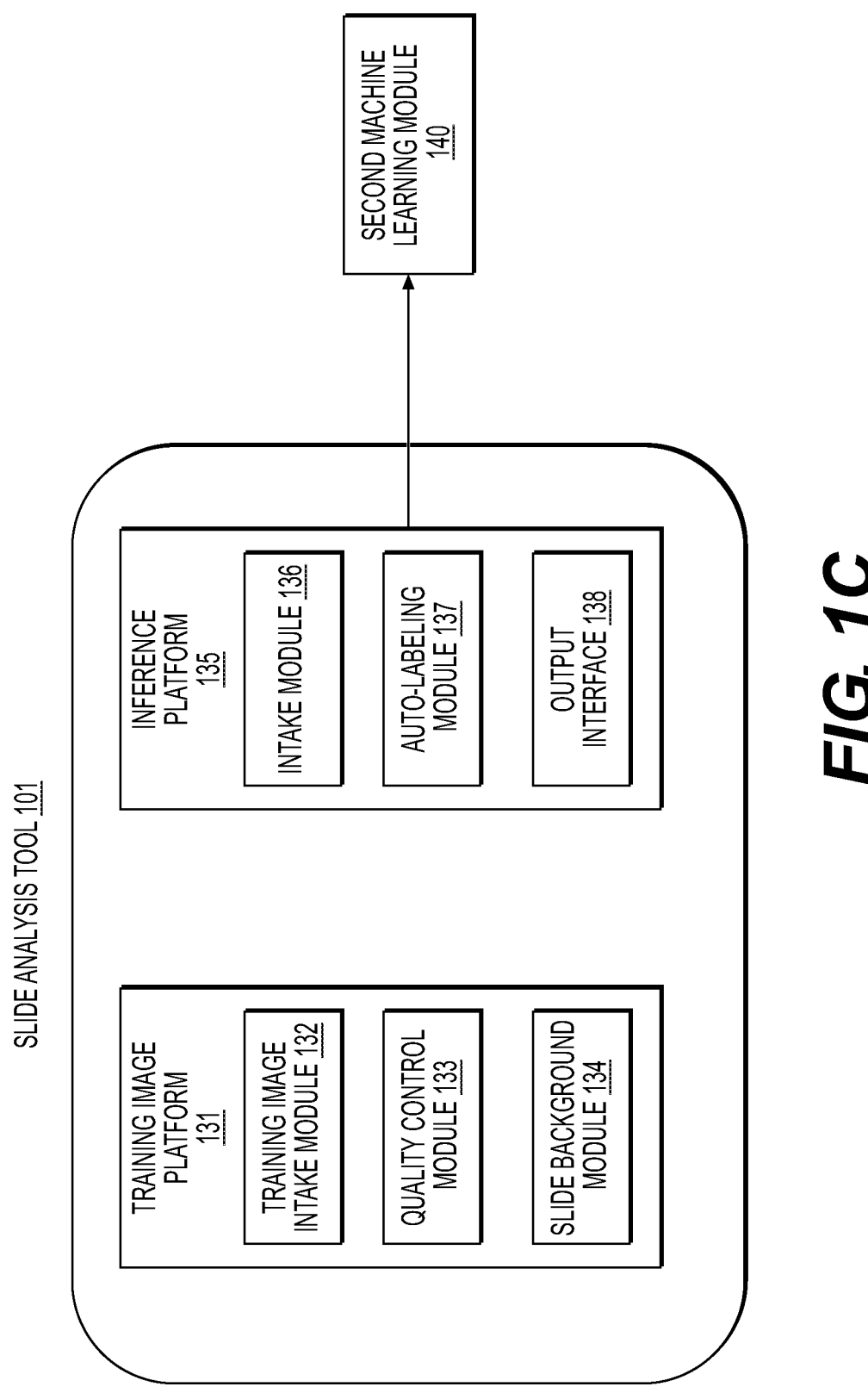
FIG. 1C illustrates an exemplary block diagram of a slide analysis tool, according to techniques presented herein.

FIG. 1C illustrates an exemplary block diagram of the slide analysis tool 101 of the system of FIG. 1A, according to certain embodiments of the present disclosure. The slide analysis tool 101 may include a training image platform 131 (e.g., that may include a training image intake module 132, a training quality control module 133, and a slide background module 134) and/or a target image platform 135 (e.g., that may include an intake module 136, an auto-labeling module 137, and an output interface 138).

The training image platform 131 may include one or more computing devices capable of, e.g., creating or receiving training images that are used to train a machine learning model to effectively analyze and classify digital pathology images. For example, the training images may be received from the server systems 110, the physician servers 121, the hospital servers 122, the clinical trial servers 123, the research lab servers 124, and/or the laboratory information systems 125. Images used for training may be obtained from real sources (e.g., humans, animals, etc.) or may come from synthetic sources (e.g., graphics rendering engines, three dimensional (3D) models, etc.). Examples of digital pathology images may include (a) digitized slides stained with a variety of stains, such as H&E, Hematoxylin alone, immunohistochemistry (IHC), molecular pathology, etc.; and/or (b) digitized tissue samples from a 3D imaging device, such as microcomputed tomography (microCT).

The training image intake module 132 may include one or more computing devices capable of, e.g., creating, receiving, or analyzing a dataset comprising one or more training datasets corresponding to one or more health variables and/or one or more data variables. For example, the training datasets may be received from the server systems 110, the physician servers 121, the hospital servers 122, the clinical trial servers 123, the research lab servers 124, and/or the laboratory information systems 125. This dataset may be kept on a digital and/or electronic storage device. The training quality control module 133 may include one or more computing devices capable of, e.g., determining whether the training images have a sufficient level-of-quality for training a machine learning model. For example, the quality control module 133 may receive and/or record subcategories classifications of received training images. In one embodiment, the quality control module 133 may receive information pertaining to what Gleason scores are present on the received images. An example may be that the quality control module 133 may note that a received slide only has cancer with a Gleason 3 score present. The slide background module 134 may include one or more computing devices capable of, e.g., identifying whether a set of individual cells belong to a cell of interest or a background of a digitized image. Upon identification of background portions of a training image, the slide background module 134, the slide background module 134 may be capable of removing background portions from training images.

The target image platform 135 may include one or more computing devices capable of, e.g., receiving a target image and applying a machine learning model to the received target image to determine a characteristic of a target data set. For example, the target data may be received from the server systems 110, the physician servers 121, the hospital servers 122, the clinical trial servers 123, the research lab servers 124, and/or the laboratory information systems 125. The intake module 136 may include one or more computing devices capable of, e.g., receiving a target dataset corresponding to a target health variable or a data variable. Auto-labeling module 137 may include one or more computing devices capable of, e.g., applying a machine learning model to the target dataset to identify regions within each subset of the plurality of electronic medical images associated with the subcategory. The auto-labeling module 137 may be capable of outputting a segmentation map identifying all subcategories within the inputted slides. In one embodiment, the auto-labeling module 137 may be imported or accessed through the network 120 and not located within the slide analysis tool 101. An exemplary auto-labeling module 137 may be a machine learning system capable of identifying cancer.

The output interface 138 may include one or more computing devices capable of, e.g., outputting information about the target data and the determined relationship (e.g., to a screen, monitor, storage device, web browser, etc.). The output interface 138 may output sets of digital medical images with corresponding segmentation maps. For example, the output interface 138 may output sets of digital medical slides that are labeled (e.g., with a segmentation map) and only contain a single subcategory. In one embodiment, these slides may be utilized to train a second machine learning system (e.g., the second machine learning module 140). The machine learning systems that may be utilized include, but are not limited to, systems that train convolutional neural networks on local windows for each detection location, vision transformers, semantic segmentation network etc.

Any of the above devices, tools, and modules may be located on a device that may be connected to an electronic network 120, such as the Internet or a cloud service provider, through one or more computers, servers, and/or handheld mobile devices.

Figure 2:
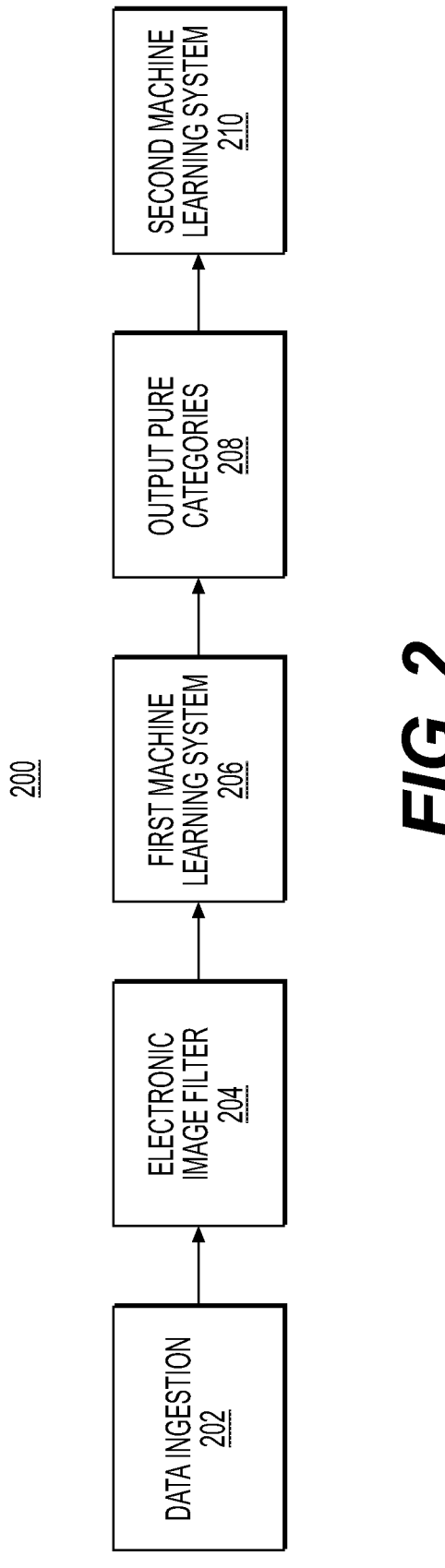
FIG. 2 is a flow diagram illustrating an exemplary process for using a trained system to perform auto-labeling, according to techniques presented herein.

FIG. 2 is a flow diagram illustrating an exemplary process 200 for using a trained system to perform auto-labeling, according to techniques presented herein. The training of the system may be implemented by the slide analysis tool 101 of the tissue viewing platform 100. In one example, the system may import a first trained system capable of identifying and mapping a top-level category (e.g., cancer). In another example, the system may include the first trained system (e.g., the auto-labeling module 137). The system may then be capable of providing outputted images from the first trained system to a second trained system (e.g., the second machine learning module 140).

At step 202, the system (e.g., intake module 136) may first include data ingestion. Step 202 may include receiving one or more digital medical images (e.g., WSI of an autopsy pathology specimen, magnetic resonance imaging (MRI), computed tomography (CT), positron emission tomography (PET), mammogram, etc.) into a digital storage device 109 (e.g., hard drive, network drive, cloud storage, RAM, etc.). The data ingestion may further receive data such as the subcategories of each of the inputted digital medical images. For example, the imported plurality of digital medical images (e.g., WSIs) may include metadata that identifies the types of sub-categories present within the slide (e.g., for prostate cancer WSIs, the slides may be marked to indicate what Gleason patterns are present on the WSIs). For example, an inputted slide may include metadata describing all Gleason scores present on the corresponding inputted slide. For example, the metadata may note that a particular slide has the sub-categories of Gleason pattern 3 and 4 present on a particular slide.

At step 204, the system (e.g., the slide filter 112) may filter the digital medical images received at step 202. In particular, the system may filter the digital medical images to determine which of the digital medical images have only a single sub-category ("pure categories") present on the particular slide. For instance, the system may filter digital medical images with prostate cancer to determine all of the plurality of digital medical images that only have Gleason score 3 present. Filtering may be performed though an algorithm that is capable of receiving the metadata. At step 204, the pure categories may be grouped and labeled together. For example, the system may save separate groups of pure categories such as all digital medical images that only contain Gleason pattern 3 and a separate group of digital medical images that only contain Gleason pattern 4. In this example, the outputted pure categories may include digital medical images with a Gleason score 3+3, 4+4, and 5+5.

In another example, the system may receive at step 202, only digital medical images that contain single sub-categories (e.g., filtering may have taken place prior to the images being received by the system).

At step 206, the system may input the filtered slides into a first machine learning system (e.g., the auto-labeling module 137). The first machine learning system may either receive as input pure category slides. Alternatively, the first machine learning system may receive as input metadata indicating the pure categories from step 202. Next, the first machine learning system may then request/receive pure categories at step 202 based on the metadata.

The first trained machine learning system may be trained to identify a particular category (e.g., cancer) and output a segmentation mask. The first trained machine learning system main be trained by supervised training. The filtered slides received at step 206 may be only pure category digital images. Once inputted into the first machine learning module, the machine learning system may mark each segmentation mask with the corresponding sub-category that each slide included. Thus, the outputted digital medical images may be labeled with their distinct granular categories.

At step 208, the system (e.g., the output interface 138) may output segmentation masks created by the first machine learning system. The output may further include corresponding metadata indicating the pure categories to which each outputted digital image belongs. These may be outputted to a second machine learning system (e.g., the second machine learning module 140). The second machine learning system may either be a part of the system, or separate from the system and accessible via network 120.

At step 210, the system (e.g., the second machine learning module 140) may then train a second machine learning system to identify the sub-categories using the segmentation masks outputted from the first machine learning system. For example, the second machine learning system may use the pure category digital medical images to train the system how to identify different sub-categories. The second machine learning system may thus be built to have aggregated fine-grained categories.

Figure 3A:
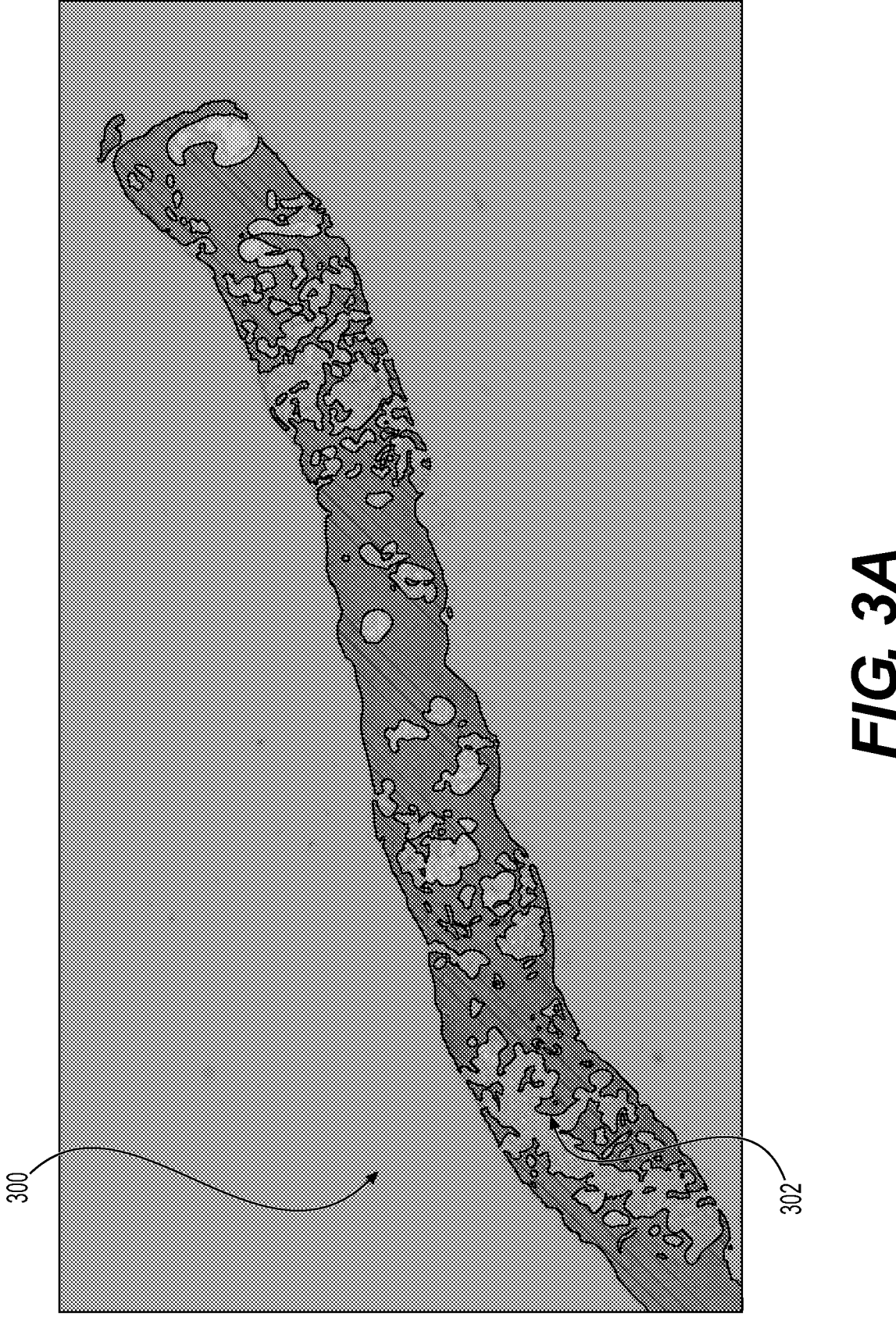
FIG. 3A is an exemplary digital medical image of tissue displaying the location of cancer, according to techniques presented herein.
Figure 3B:
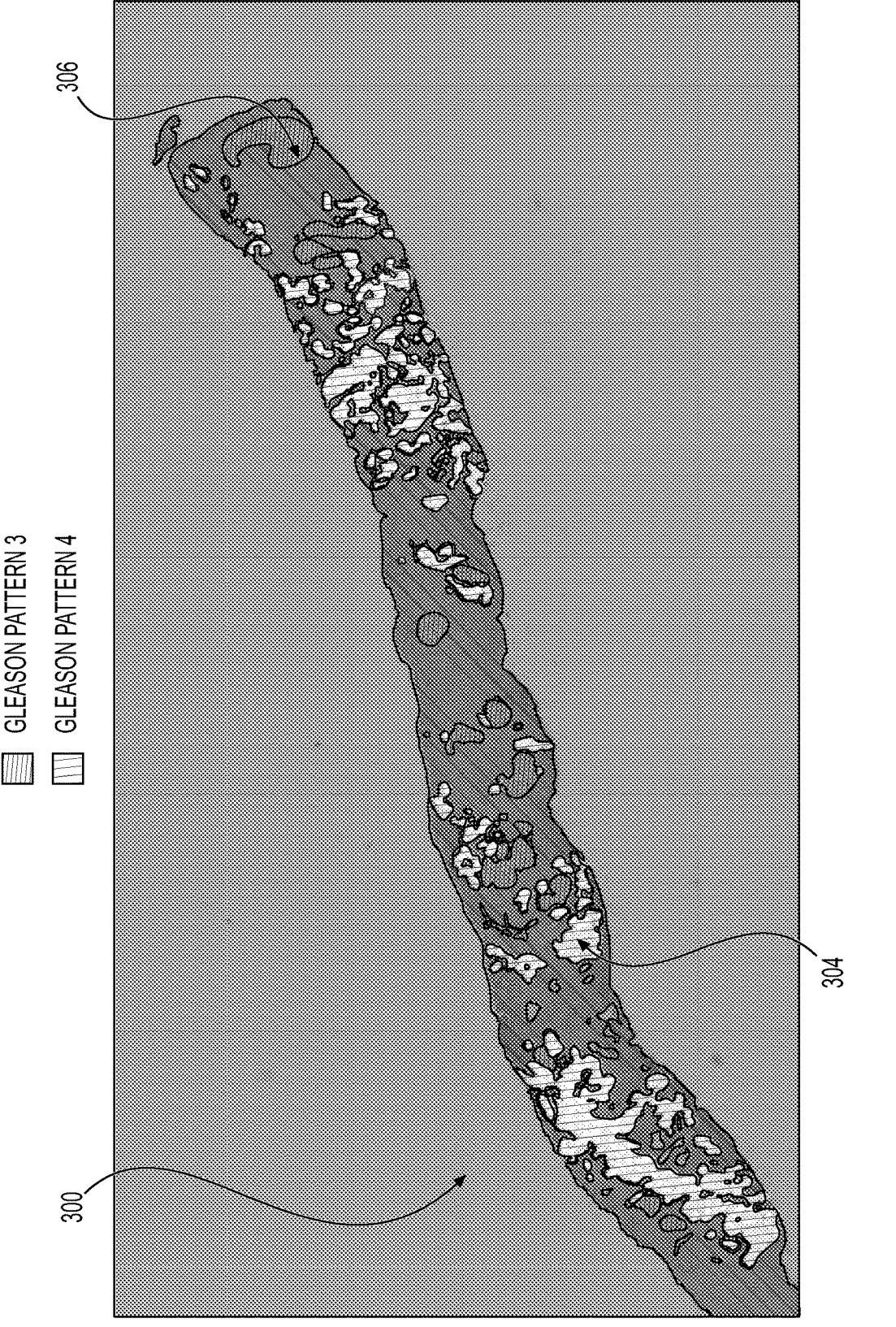
FIG. 3B is an exemplary digital medical image of tissue displaying the distinct grades of cancer, according to techniques presented herein.

FIG. 3A is an exemplary digital medical image of tissue displaying the location of cancer, according to techniques presented herein. FIG. 3B is an exemplary digital medical image of tissue displaying the distinct grades of cancer, according to techniques presented herein. FIG. 3A displays a tissue 300 that has cancer 302 detected. FIG. 3B displays tissue 300 that has cancer patterns with distinct grades 304 and 306 indicating different outcomes or different kinds of cancer. FIG. 3B may thus be a more detailed segmentation mask of the cancer depicted in FIG. 3A including distinct categories. The distinct grades are illustrated by the differently markings on the bottom image, differentiated by the legend. The system described herein may be capable of creating a machine learning system capable of identifying the subcategories displayed in FIG. 3B. In one technique, an art detection system may be created that can infer the general class, but in some cases there might not be robust data for the fine-grained categories.

FIG. 3A may be an exemplary output of what the first machine learning system may output at step 206 (e.g., only an overall category is identified such as cancer). FIG. 3B may be an example of what the trained second machine learning system at 210 may output.

The system and techniques described herein may use a detection system that infers the location of the top-level category, e.g., cancer. Next, the system may utilize "pure categories" digital medical images that only have one of the fine-grained class/grades present on the digital medical images. The system (e.g., a first machine learning system) may then auto label these pure categories. The labeled pure categories may then be utilized for training of fine-grained classifiers of the distinct features, e.g., kinds of cancer, by a second machine learning system. The system may allow for fine-grained information for the entire image to propagate to the appropriate locations in an image using the detection system to identify the relevant regions.

Figure 4:
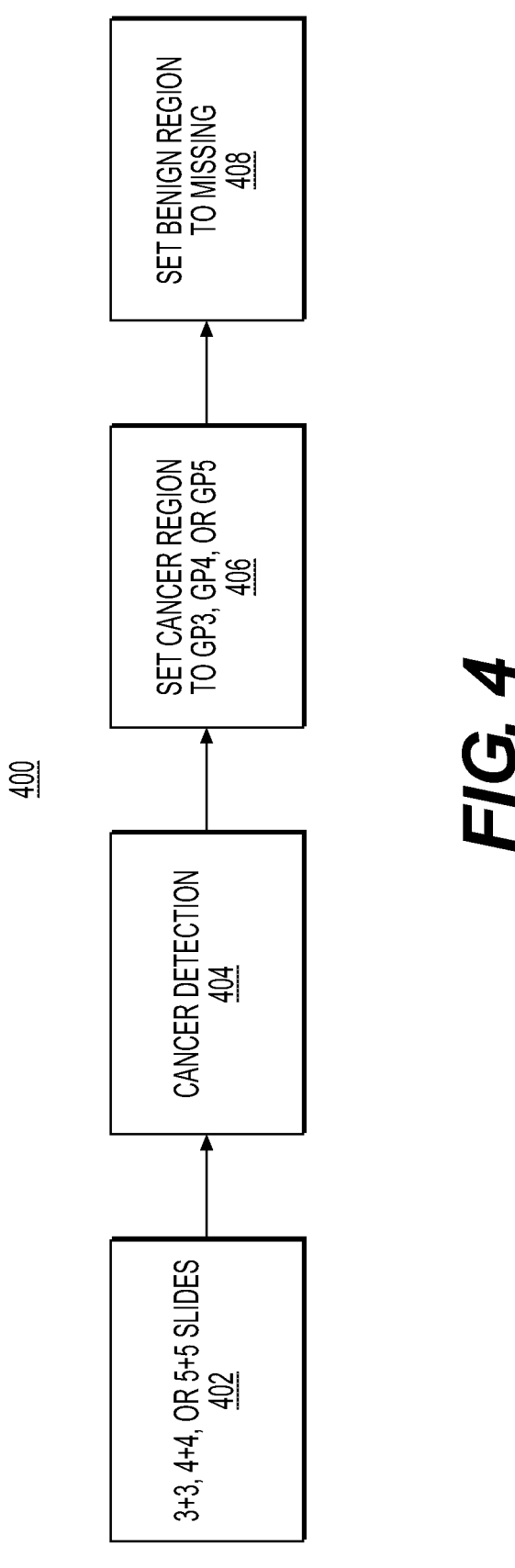
FIG. 4 is a flow diagram illustrating an exemplary process for using a trained system to auto-label digital medical images related to prostate cancer, according to techniques presented herein.

FIG. 4 depicts an exemplary overall workflow 400 of the system and techniques discussed herein on prostate cancer. First, at step 402, the system may receive datasets of digital medical images of tissue with prostate cancer. The dataset may then be filtered to contain only "pure cases" including Gleason score 3+3, 4+4, and 5+5. Filtering may be performed by an algorithm utilizing corresponding metadata for the inputted digital medical images.

Next at step 404, once pure cases are identified, the system may identify (e.g., through a cancer detector model) all the cancer locations in the image. The system may utilize a machine learning system to identify locations of the cancer.

At step 406, the system may create a segmentation mask. Each digital medical image's cancer region is composed of pure cases, allowing the system to assign the subordinate category/grade to all the cancer regions in the image. This approach may enable the images to be automatically labeled/graded.

At step 408, the system may set benign regions to missing. The system may utilize a trained detector, which has the ability to identify the regions in the image that belong to the general category, e.g., cancer versus non-cancer. The non-cancer regions may be labeled as benign. This may be performed by the same detector used in steps 404 and 406.

Once the data is labeled automatically, the segmented digital medical images may be outputted and used to train a second machine learning/AI (Artificial Intelligence) model in a supervised fashion. The outputs may occur automatically and include labeled images with the granular categories/grades.

FIG. 5A is a flowchart illustrating an example method for training a system to auto-label digital medical images, according to one or more embodiments. The method 500 of FIG. 5A depicts steps that may be performed by, for example, the slide analysis tool 101. Alternatively, the method 500 may be performed by an external system.

At step 502, the system (e.g., the slide analysis tool 101) may receive and/or determine a trained detection system (e.g., the auto-labeling module 137) capable of identifying the regions of an image with the general category of interest, e.g., cancer, into digital storage 109 (RAM, hard drive, cloud storage, etc.)

At step 504, the system (e.g., the intake module 136) may receive a collection of digital medical images (e.g., WSIs) with each of the subordinate categories identified at the image level, but not at a local level. This information may be included as metadata.

At step 506, the system (e.g., the slide filter 112) may filter the collection of images to identify the images that are "pure" and have only a single sub-ordinate category within them. These images may be referred to as pure categories.

At step 508, the system may run/implement the detection system from step 502 on each of the pure categories digital medical images and assign the subordinate category to all the locations detected. This may include creating a segmentation map with the location of all sub-categories on each of the received digital medical images. The system may save the annotations for these images to storage. The segmentation maps may then be outputted to a second machine learning system (e.g., the second machine learning module 140).

At step 510, the system may train a second machine learning system (e.g., the second machine learning module 140) to detect the subordinate categories using the auto-labeled dataset. The machine learning systems that may be utilized include, but are not limited to, systems that train convolutional neural networks on local windows for each detection location, vision transformers, semantic segmentation network etc.

At step 512, the system may save the trained system to digital storage 109.

Figure 5B:
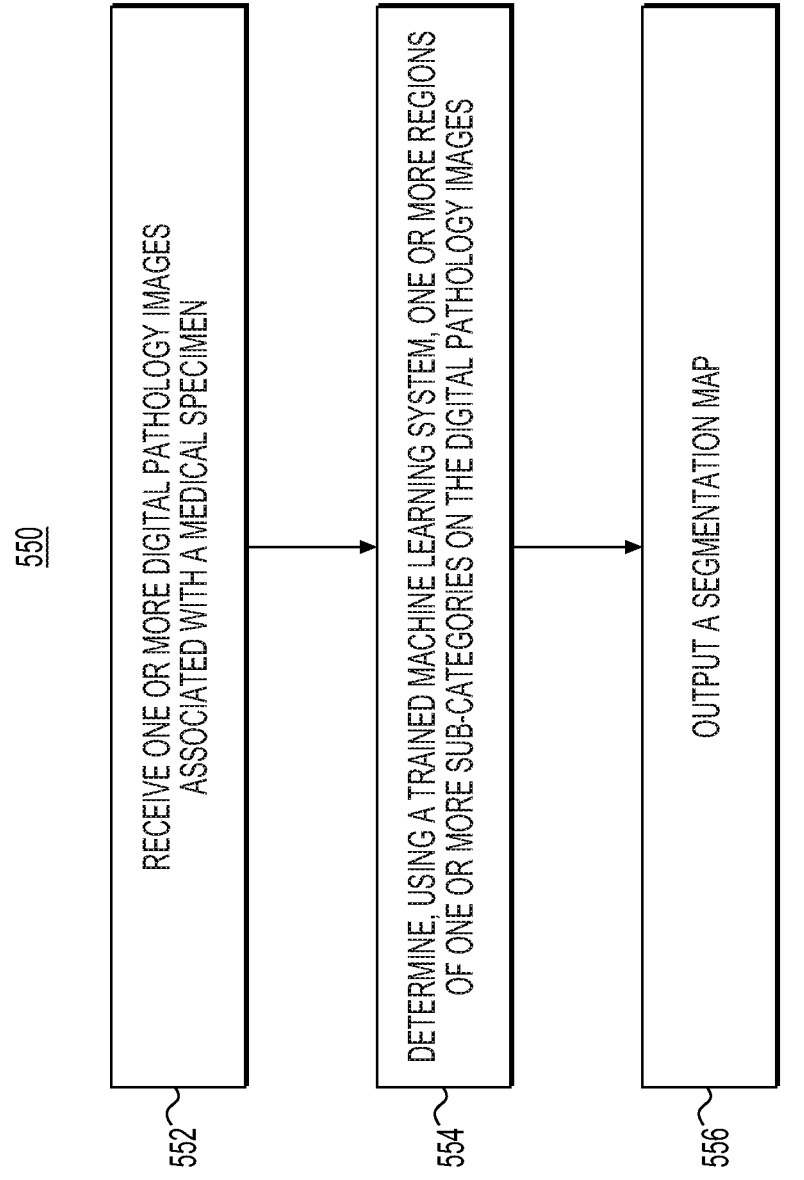
FIG. 5B is a flowchart illustrating an example method for using a system to auto-label digital medical images, according to one or more embodiments.

FIG. 5B is a flowchart illustrating an example method for using a system to auto-label digital medical images, according to one or more embodiments. The exemplary method 550 (e.g., steps 552-556) of FIG. 5B depicts steps that may be performed by, for example, the second machine learning module 140. These steps may be performed automatically or in response to a request from a user (e.g., a pathologist, a department or laboratory manager, an administrator, etc.). Alternatively, the method 550 may be performed by any machine learning system capable of receiving the segmentation maps from step 508 such as device 900.

At step 552, the trained system (e.g., the second machine learning module 140) may receive a plurality of digital medical images of pathology slides associated with pathology cases. These digital medical images may include images with multiple sub-categories (e.g., multiple Gleason score sections present).

At step 554, the trained system may determine one or more regions of one or more sub-categories of the received digital medical images of step 552. This may include creating segmentation maps of the sub-categories. Further, the system may be capable of determining and storing the total area of each sub-category within a slide. This may be saved as corresponding metadata with each slide. Further, this information may be utilized to determine a score prediction for a slide. For example, a Gleason score may be determined based on the proportions of Gleason pattern 3, 4, and 5 present.

At step 556, the trained system may output the segmentation map. This may include saving the segmentation map to electronic storage. Further this may include outputting the segmentation map to a user interface (e.g., to a screen, monitor, storage device, web browser, etc.). Further, corresponding information such as a diagnosis or percentages of subcategories may be outputted with the segmentation map.

Figure 6B:
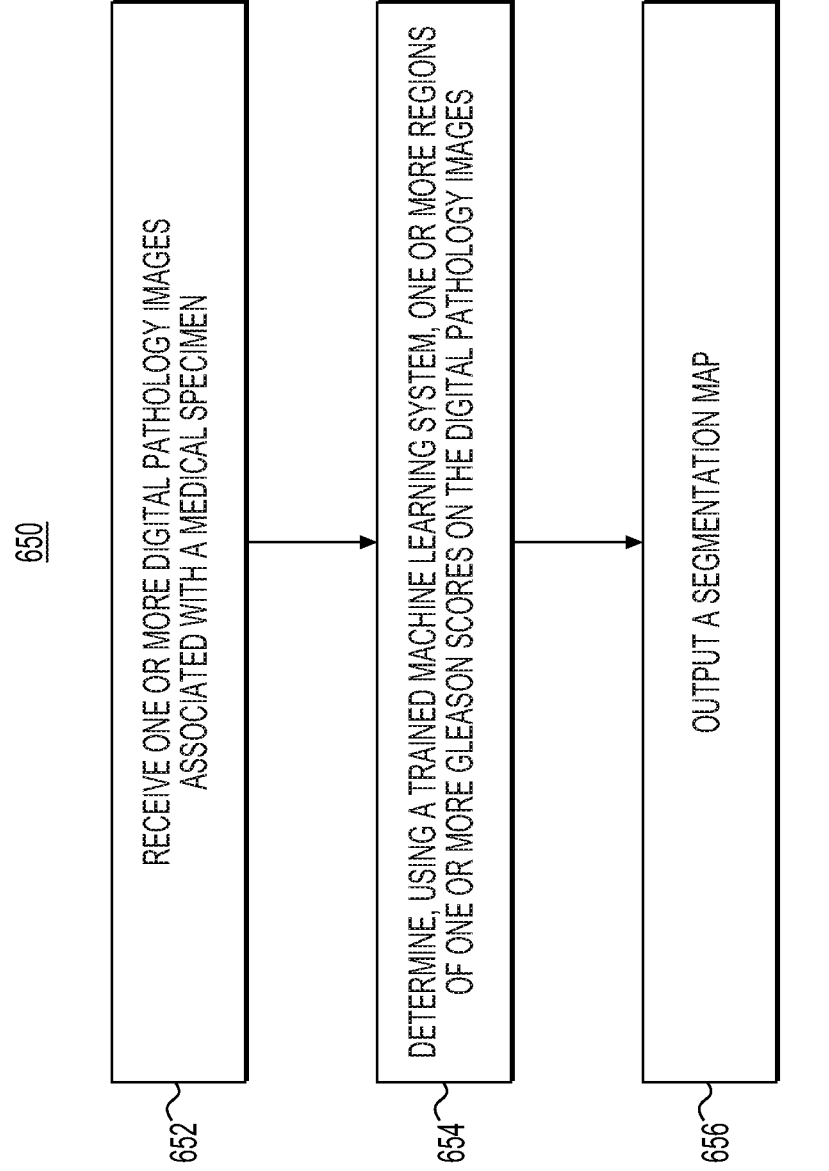
FIG. 6B is a flowchart illustrating an example method for using a system to auto-label Gleason pattern localization on digital medical images, according to one or more embodiments.

In one example of the system, the system may be create a trained machine learning system to determine auto-labeling pattern localization and grade group prediction. In this example, the system may identify different types of Gleason pattern in pure Gleason score cases, generate segmentation masks using them, and train a model to classify an image tile into one of Gleason pattern classes (as shown in FIGS. 6A and 6B). If the system is provided a digital medical image (e.g., a WSI), all tissue tiles within the WSI may be classified into one of Gleason pattern classes and the slide-level Gleason score/group grade is obtained by computing the proportion of each Gleason pattern in the WSI.

FIG. 6A is a flowchart illustrating an example method for training a system to auto-label Gleason patterns on digital medical images, according to one or more embodiments. The method 600 of FIG. 6A depicts steps that may be performed by, for example, the slide analysis tool 101. Alternatively, the method 600 may be performed by an external system.

At step 602, the system (e.g., the Receive/determine a trained detection system capable of identifying the regions of an image/WSI with prostate cancer, into digital storage (RAM, hard drive, cloud storage, etc.)

At step 604, the system (e.g., the intake module 136) may receive a collection of digital medical images with each of the Gleason patterns (e.g. 3, 4, or 5) identified at the image level, but not at a local level. In another example, metadata corresponding with each of the inserted digital medical images may be inputted to the system at this step.

At step 606, the system (e.g., the slide filter 112) may filter the collection of images to identify the images that are "pure" and have only a single sub-ordinate category within them. The system may utilize any of the filter algorithm discussed herein. The system may identify the digital medical images with a Gleason score of 3+3, 4+4, and 5+5 as pure category images. These images may then be inputted/sent to a first machine learning system (e.g., the auto-labeling module 137). The first machine learning module may be previously trained to identify the presence of cancer on a digital medical image.

At step 608, the system may run the detection system (e.g., the auto-labeling module 137) on each of the pure category images and assign the subordinate category to all the locations detected. This may include creating a segmentation mask of all identified cancer within each of the pure categories. The system may then save the segmentation mask/annotations for these images to one or more electronic storage devices 109.

Next, at step 610, the system may train a machine learning system (e.g., the second machine learning module 140) to detect and classify all Gleason patterns on a digital medical image using the auto-labeled dataset from step 608. Further, the system may be trained to determine and output a Gleason score for the WSI based on the proportions of each Gleason pattern in the WSI. The second trained machine learning systems that may be utilized include, but are not limited to, systems that train convolutional neural networks on local windows for each detection location, vision transformers, semantic segmentation network, etc.

Next, as step 612, the system may save the trained second machine learning system to digital storage 109.

FIG. 6B is a flowchart illustrating an example method for using a system to auto-label Gleason pattern localization on digital medical images, according to one or more embodiments. The exemplary method 650 (e.g., steps 652-656) of FIG. 6B depicts steps that may be performed by, for example, the second machine learning module 140. These steps may be performed automatically or in response to a request from a user (e.g., a pathologist, a department or laboratory manager, an administrator, etc.). Alternatively, the method 650 may be performed by any machine learning system capable of receiving the segmentation maps from step 608 such as device 900.

At step 652, the trained system (e.g., the second machine learning module 140) may receive a plurality of digital medical images of pathology slides associated with pathology cases. These digital medical images may include images with one or more Gleason sub-categories present.

At step 654, the trained system may determine one or more regions of open or more sub-categories of Gleason pattern of the received digital medical images of step 652. This may include creating segmentation maps of the Gleason scores present (see FIGS. 3B and 7B as examples). Further, the system may be capable of adding the total area of each Gleason score within a digital medical image. This information may be utilized to determine a Gleason score prediction for a digital medical image. For example, a Gleason score may be determined based on the proportions of Gleason pattern 3, 4, and 5 present. For instance, if the system determines that the largest amount of cancer present is pattern 3 and that there is Gleason pattern 4 present and no Gleason pattern 5, the system may output a Gleason score of 3+4.

At step 656, the trained system may output the segmentation map. This may include saving the segmentation map to electronic storage. Further this may include outputting the segmentation map to a user interface (e.g., to a screen, monitor, storage device, web browser, etc.).

Figure 7A:
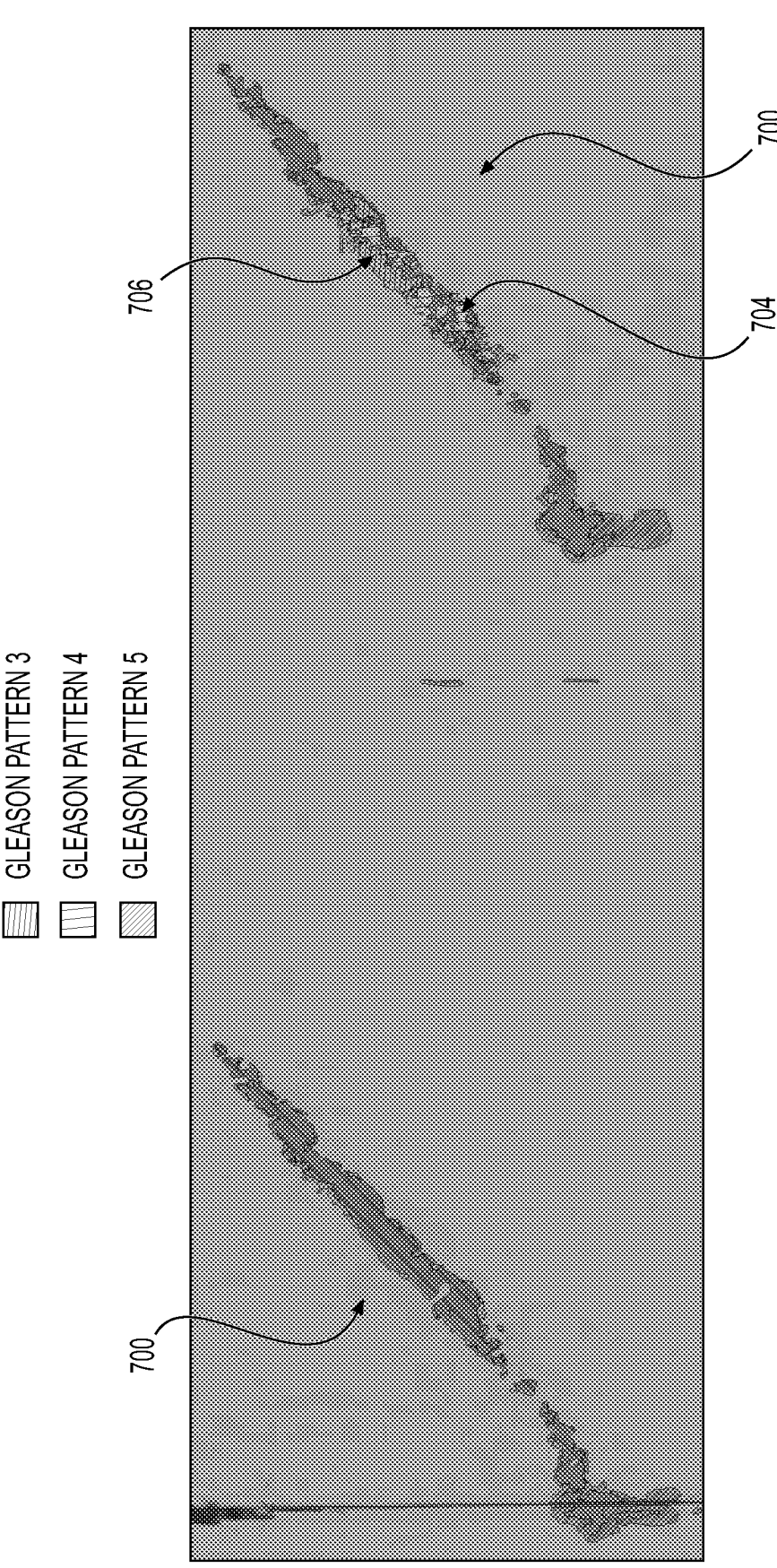
FIG. 7A is an exemplary digital medical image of tissue displaying the location of cancer, according to techniques presented herein.

FIG. 7A is an exemplary digital medical image of tissue displaying the location of cancer, according to techniques presented herein.

Figure 7B:
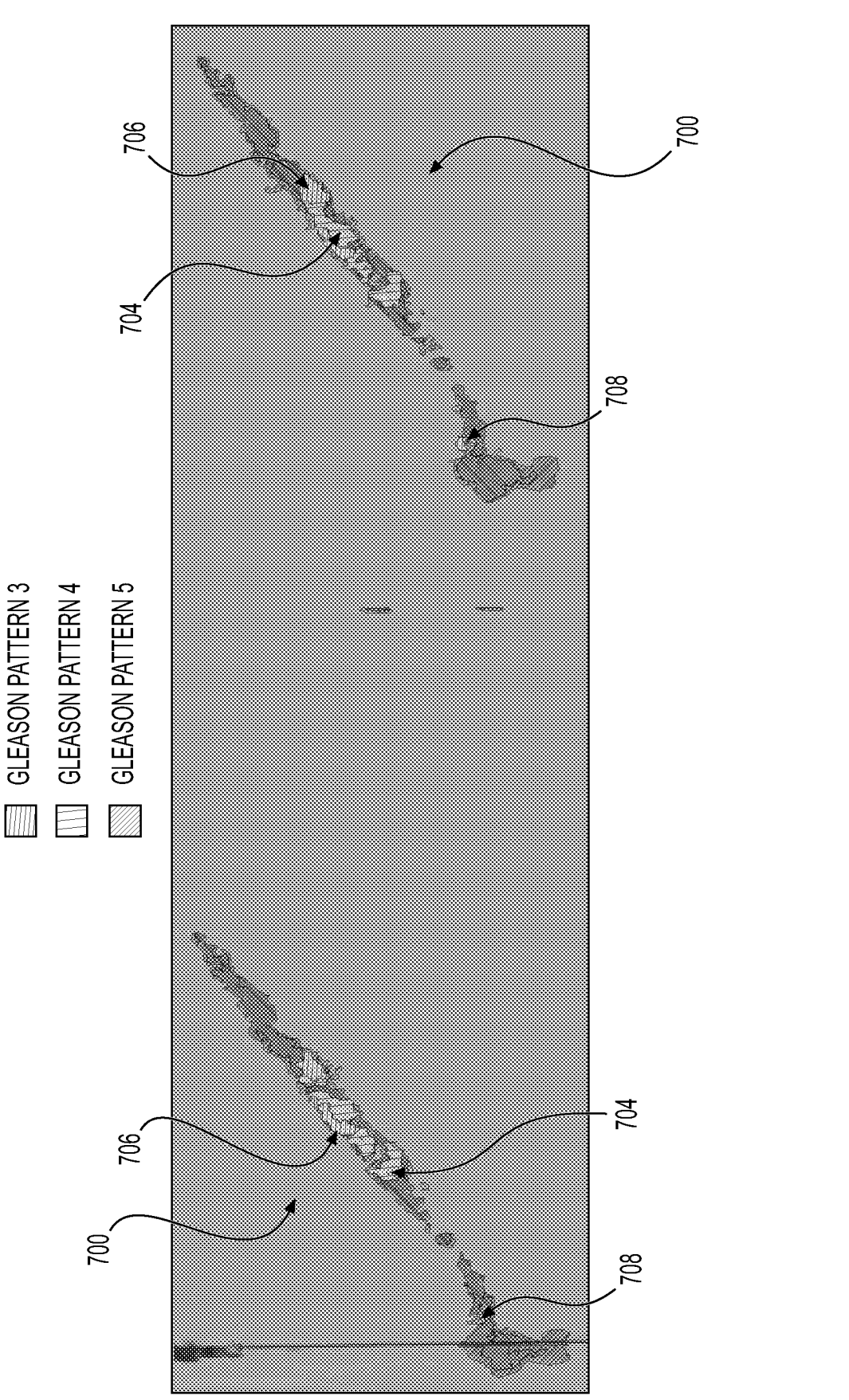
FIG. 7B is an exemplary digital medical image of tissue displaying the location of cancer, according to techniques presented herein.

FIG. 7B is an exemplary digital medical image of tissue displaying the distinct grades of cancer, according to techniques presented herein.

FIG. 7A displays tissue 700 first with (right tissue) and then without (left tissue) a segmentation mask. The segmentation mask of FIG. 7A may be hand drawn or created by a user. The annotated segmentation mask may display Gleason pattern 3 at 704 and Gleason pattern 4 at 706. FIG. 7B may display the tissue 700 with a segmentation mask created the second machine learning module 140 or a similar machine learning model that has been trained using the techniques discussed in FIG. 6A. The segmentation mask may display Gleason pattern 3 at 704, Gleason pattern 4 at 706, and Gleason pattern 5 at 708.

Further, the exemplary techniques described herein may be used for auto-labeling morphological pattern localization under domain shift. Domain shift is a phenomenon in which the distribution of training data is different from production data. Domain shift may happen under different conditions. For instance, scanning the same slide using two different scanners may generate two WSIs that may be different from each other from the model's perspective. Likewise, scanning the slide using the same scanner with two different configurations may generate slightly different WSIs. The accuracy of deep models may decrease under domain shift. A remedy to domain shift is to re-train/fine-tune the model using more diverse data.

Given a trained model for localizing a morphological pattern of interest (e.g., a specific kind of breast cancer, nerve, muscles, etc.), the model may be run on the data with domain shift to generate segmentation masks for each pattern of interest. The masks could be refined further using human experts and used for retraining/fine-tuning the model. In this embodiment, generating initial segmentation masks using the model and revising them by human experts may be faster than generating segmentation masks solely by human experts.

The system described herein may receive a trained detection system capable of identifying the regions of an image with the general category of interest, e.g., a morphological pattern of interest, into digital storage (RAM, hard drive, cloud storage, etc.). Next, the system may receive a collection of domain-shifted images/WSI with each of the subordinate categories identified at the image level, but not at a local level. Next, the system may filter the collection of images to identify the images that are "pure" and have only a single sub-ordinate category within the image. Next, the system may run the detection system on each of the pure images, assign the subordinate category to all the locations detected, and create an initial segmentation mask. Next, the segmentation masks may be reviewed by human experts. The segmentation masks may then be saved for training purposes. Last, a second machine learning system may be trained to detect the subordinate categories using the auto-labeled dataset.

In another example of the system, the auto-labeling system may be trained to perform Gleason pattern localization under domain shift. This may include performing all steps from FIG. 6A, but utilizing digital medical images that include domain shifts at step 604.

FIG. 8 is a flowchart illustrating an example method 800 for optimizing the order of cases displayed to one or more users.

At step 802, the system may determine a first machine learning system, the first machine learning system having been trained to identify regions of electronic medical images.

At step 804, the system may receive a plurality of electronic medical images, each of the electronic medical images being associated with one or more subcategories.

At step 806, the system may determine a subset of the plurality of electronic medical images that are associated with only one subcategory of the one or more subcategories At step 808, the system may provide the subset of the plurality of electronic medical images to the first machine learning system, the first machine learning system identifying regions within the subset of the plurality of electronic medical images associated with the subcategory.

At step 810, the system may train a second machine learning system, using the identified regions and the subset of the plurality of electronic medical images.

Figure 9:
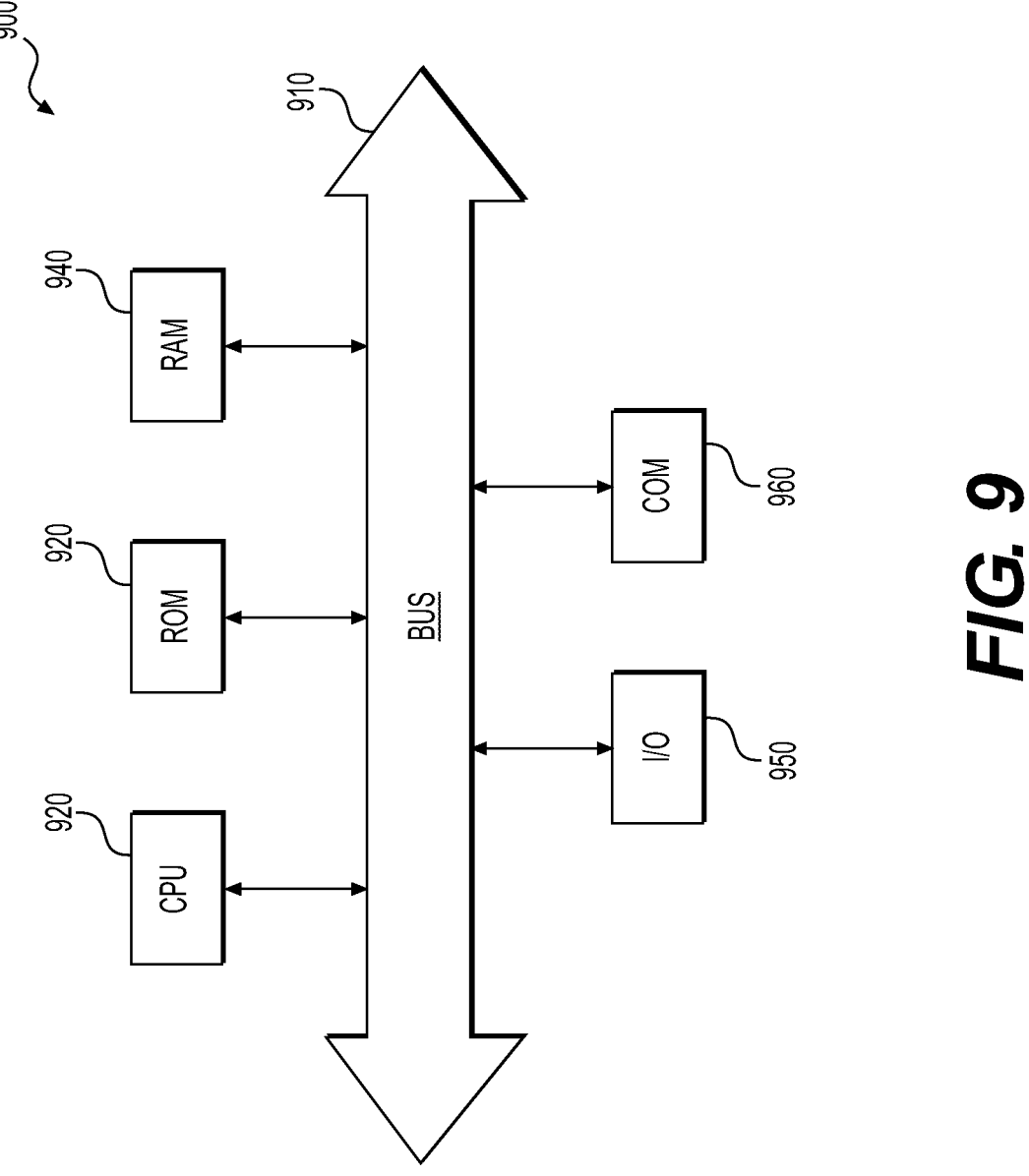
FIG. 9 depicts an example of a computing device that may execute techniques presented herein, according to one or more embodiments.

As shown in FIG. 9, device 900 may include a central processing unit (CPU) 920. CPU 920 may be any type of processor device including, for example, any type of special purpose or a general-purpose microprocessor device. As will be appreciated by persons skilled in the relevant art, CPU 920 also may be a single processor in a multi-core/multi-processor system, such system operating alone, or in a cluster of computing devices operating in a cluster or server farm. CPU 920 may be connected to a data communication infrastructure 910, for example a bus, message queue, network, or multi-core message-passing scheme.

Device 900 may also include a main memory 940, for example, random access memory (RAM), and also may include a secondary memory 930. Secondary memory 930, for example a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 930 may include similar means for allowing computer programs or other instructions to be loaded into device 900. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 900.

Device 900 also may include a communications interface ("COM") 960. Communications interface 960 allows software and data to be transferred between device 900 and external devices. Communications interface 960 may include a modem, a network interface (such as an Ethernet card), a communications port, a PCMCIA slot and card, or the like. Software and data transferred via communications interface 960 may be in the form of signals, which may be electronic, electromagnetic, optical or other signals capable of being received by communications interface 960. These signals may be provided to communications interface 960 via a communications path of device 900, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 900 may also include input and output ports 950 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically may be grouped together to perform a function or group of related functions. Like reference numerals are generally intended to refer to the same or similar components. Components and/or modules may be implemented in software, hardware, or a combination of software and/or hardware.

The tools, modules, and/or functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution. The foregoing general description is exemplary and explanatory only, and not restrictive of the disclosure. Other embodiments may be apparent to those skilled in the art from consideration of the specification and practice of the invention disclosed herein. It is intended that the specification and examples be considered as exemplary only.

What is claimed is:

1. A computer-implemented method for processing electronic medical images, comprising:
   receiving a plurality of electronic medical images, each of the electronic medical images being associated with one or more subcategories of health grades;
   determining a first machine learning system of a plurality of machine learning training systems, the first machine learning system having been trained to identify one subcategory of the one or more subcategories;
   providing the plurality of electronic medical images to the first machine learning system to determine a subset of the plurality of electronic medical images associated with the one subcategory that the first machine learning system has been trained to identify;
   training a second machine learning system, using the subset of the plurality of electronic medical images; and
   repeating the determining, providing and training steps with remaining machine learning systems of the plurality of machine learning training systems, each of the remaining machine learning systems being trained identify a different subcategory of the one or more subcategories.

2. The method of claim 1, wherein the subcategories are Gleason pattern scores.

3. The method of claim 2, wherein the second machine learning system may classify tissue within new electronic images into one of the Gleason pattern scores.

4. The method of claim 3, wherein the second machine learning system outputs a slide level Gleason score based on proportions of each Gleason score assigned to the tissue within the electronic images.

5. The method of claim 1, wherein the first machine learning system creates a segmentation mask for each subset of the plurality of electronic medical images associated with each subcategory.

6. The method of claim 1, wherein the second machine learning system is capable of identifying one or more subcategories on additional electronic medical images.

7. The method of claim 1, wherein the plurality of electronic medical images are images that have had a domain shift applied.

8. A system for processing electronic medical images, the system comprising:
   at least one memory storing instructions; and
   at least one processor configured to execute the instructions to perform operations comprising:
      receiving a plurality of electronic medical images, each of the electronic medical images being associated with one or more subcategories of health grades;
      determining a first machine learning system of a plurality of machine learning training systems, the first machine learning system having been trained to identify one subcategory of the one or more subcategories;
      providing the plurality of electronic medical images to the first machine learning system to determine, a subset of the plurality of electronic medical images associated with the one subcategory that the first machine learning system has been trained to identify;
      training a second machine learning system, using the subset of the plurality of electronic medical images; and
      repeating the determining, providing and training steps with remaining machine learning systems of the plurality of machine learning training systems, each of the remaining machine learning systems being trained identify a different subcategory of the one or more subcategories.

9. The system of claim 8, wherein the subcategories are Gleason pattern scores.

10. The system of claim 9, wherein the second machine learning system may classify tissue within new electronic images into one of the Gleason pattern scores.

11. The system of claim 10, wherein the second machine learning system outputs a slide level Gleason score based on proportions of each Gleason score assigned to the tissue within the electronic images.

12. The system of claim 8, wherein the first machine learning system creates a segmentation mask utilizing the identified regions.

13. The system of claim 8, wherein the second machine learning system is capable of identifying one or more subcategories on additional electronic medical images.

14. The system of claim 8, wherein the plurality of electronic medical images are images that have had a domain shift applied.

15. A non-transitory computer-readable medium storing instructions that, when executed by a processor, perform operations processing electronic digital medical images, the operations comprising:

receiving a plurality of electronic medical images, each of the electronic medical images being associated with one or more subcategories of health grades;

determining a first machine learning system of a plurality of machine learning training systems, the first machine learning system having been trained to identify one subcategory of the one or more subcategories;

providing the plurality of electronic medical images to the first machine learning system to determine, a subset of the plurality of electronic medical images associated with the one subcategory that the first machine learning system has been trained to identify;

training a second machine learning system, using the subset of the plurality of electronic medical images; and repeating the determining, providing and training steps with remaining machine learning systems of the plurality of machine learning training systems, each of the remaining machine learning systems being trained identify a different subcategory of the one or more subcategories.

16. The computer-readable medium of claim 15, wherein the subcategories are Gleason pattern scores.

17. The computer-readable medium of claim 16, wherein the second machine learning system may classify tissue within new electronic images into one of the Gleason pattern scores.

18. The computer-readable medium of claim 17, wherein the second machine learning system outputs a slide level Gleason score based on proportions of each Gleason score assigned to the tissue within the electronic images.

19. The computer-readable medium of claim 15, wherein the first machine learning system creates a segmentation mask utilizing the identified regions.

20. The computer-readable medium of claim 15, wherein the second machine learning system is capable of identifying one or more subcategories on additional electronic medical images.

\* \* \* \* \*